United States Patent
Wolfstaedter et al.

(10) Patent No.: US 9,849,611 B2
(45) Date of Patent: Dec. 26, 2017

(54) METHOD FOR PRODUCING COLLAGEN-CONTAINING SHEET MATERIAL

(71) Applicant: aap Biomaterials GmbH, Dieburg (DE)

(72) Inventors: Marco Wolfstaedter, Woerth am Main (DE); Birgit Schaefer, Babenhausen (DE); Ellen Schubert, Sulzbach (DE)

(73) Assignee: aap Biomaterials GmbH, Dieburg (DE)

(*) Notice: Subject to any disclaimer, the term of this patent is extended or adjusted under 35 U.S.C. 154(b) by 0 days.

(21) Appl. No.: 14/383,811

(22) PCT Filed: Feb. 26, 2013

(86) PCT No.: PCT/EP2013/053763
§ 371 (c)(1),
(2) Date: Sep. 8, 2014

(87) PCT Pub. No.: WO2013/135477
PCT Pub. Date: Sep. 19, 2013

(65) Prior Publication Data
US 2015/0044443 A1  Feb. 12, 2015

(30) Foreign Application Priority Data

Mar. 13, 2012 (DE) .................. 10 2012 004 842

(51) Int. Cl.
*B29C 39/00* (2006.01)
*A61L 31/04* (2006.01)
(Continued)

(52) U.S. Cl.
CPC .......... *B29C 39/003* (2013.01); *A61L 15/325* (2013.01); *A61L 15/46* (2013.01); *A61L 27/24* (2013.01); *A61L 27/44* (2013.01); *A61L 27/54* (2013.01); *A61L 27/60* (2013.01); *A61L 31/044* (2013.01); *A61L 31/16* (2013.01);
(Continued)

(58) Field of Classification Search
None
See application file for complete search history.

(56) References Cited

U.S. PATENT DOCUMENTS 3,800,792 A  4/1974  McKnight et al.
5,110,604 A  5/1992  Chu et al.
(Continued)

FOREIGN PATENT DOCUMENTS

DE     60111240 T2    3/2006
DE   102005044360 A1  3/2007
(Continued)

OTHER PUBLICATIONS

"Related U.S. Appl. No. 14/383,802", "Office Action—Restriction", Feb. 23, 2015, Publisher: USPTO, Published in: US.
(Continued)

*Primary Examiner* — Benjamin A Schiffman
(74) *Attorney, Agent, or Firm* — Kaplan Breyer Schwarz, LLP

(57) ABSTRACT

A method for producing a collagen-containing sheet material, wherein a collagen-containing suspension is dried in such a manner that the collagen settles during drying and forms a transparent skin.

8 Claims, 1 Drawing Sheet

(51) Int. Cl.
*A61L 31/16* (2006.01)
*A61L 15/32* (2006.01)
*A61L 15/46* (2006.01)
*A61L 27/24* (2006.01)
*A61L 27/44* (2006.01)
*A61L 27/54* (2006.01)
*A61L 27/60* (2006.01)
*B29K 105/00* (2006.01)
*B29K 105/04* (2006.01)
*B29K 105/16* (2006.01)
*B29K 505/00* (2006.01)
*B29K 505/14* (2006.01)
*B29L 7/00* (2006.01)

(52) U.S. Cl.
CPC ... *A61L 2300/104* (2013.01); *A61L 2300/404* (2013.01); *A61L 2300/60* (2013.01); *B29K 2089/00* (2013.01); *B29K 2105/0011* (2013.01); *B29K 2105/04* (2013.01); *B29K 2105/16* (2013.01); *B29K 2505/00* (2013.01); *B29K 2505/14* (2013.01); *B29K 2995/0097* (2013.01); *B29L 2007/008* (2013.01)

(56) References Cited

U.S. PATENT DOCUMENTS

| | | | |
|---|---|---|---|
| 5,331,092 | A | 7/1994 | Huc et al. |
| 5,785,983 | A | 7/1998 | Furlan et al. |
| 7,932,354 | B2 | 4/2011 | Heimann et al. |
| 8,580,309 | B2 | 11/2013 | Wilson et al. |
| 2003/0035786 | A1 | 2/2003 | Hendriks et al. |
| 2009/0227773 | A1 | 9/2009 | Heimann et al. |
| 2012/0225111 | A1 | 9/2012 | Scholz |
| 2015/0190550 | A1 | 7/2015 | Nusko et al. |

FOREIGN PATENT DOCUMENTS

| | | |
|---|---|---|
| DE | 102008062824 A1 | 7/2010 |
| DE | 102009059276 A1 | 6/2011 |
| DE | 102009053305 A1 | 8/2011 |
| EP | 1917982 A1 | 5/2008 |
| EP | 1635850 B1 | 8/2008 |
| EP | 2098255 A2 | 9/2009 |
| WO | 2006000304 A1 | 1/2006 |
| WO | 2011076203 A1 | 6/2011 |
| WO | 2012084072 A1 | 6/2012 |

OTHER PUBLICATIONS

Al-Bin Huang, et al., "A Trilayer Dermal Equivalent Containing Silver Nanoparticles with Enhanced Antibacterial Property", "Chinese Journal of Polymer Science", 2009, pp. 865-871, vol. 27, No. 6, Publisher: World Scientific.

"Related U.S. Appl. No. 14/383,802 Non Final Office Action", dated Apr. 29, 2015, Publisher: USPTO, Published in: US.

"Parent Patent Application in Germany No. DE 10 2012 004 842.4", "Office Action", Nov. 6, 2012, Publisher: GPTO, Published in: DE.

"Related International Application No. PCT/EP2013/053763", "International Search Report and Written Opinion", May 31, 2013, Publisher: PCT, Published in: EP.

"Related International Application No. PCT/EP2013/053764", "International Search Report and Written Opinion", dated May 31, 2013, Publisher: PCT, Published in: EP.

"Parent Patent Application in Germany: DE 10 2012 004 841.6", "Office Action", dated Nov. 6, 2012, Publisher: DPTO, Published in: DE.

Final Office Action dated Aug. 6, 2015 issued in related U.S. Appl. No. 14/383,802.

Chaloupka et al., "Nanosilver as a new generation of nanoproduct in biomedical applications", "Trends in Biotechnology", Nov. 2010, pp. 580-588, vol. 28, No. 11, Publisher: Cell Press.

Ghosh, et al, "Antimicrobial activity of highly stable silver nanoparticles embedded in agar-agar matrix as a thin film", "Carbohydrate Research", 2010, pp. 2220-2227, vol. 345, No. 2010, Publisher: Elsevier Ltd.

Machine Translation of WO 2011/076203 A1 from German to English. Original publication in German on Jun. 30, 2011, translation obtained by USPTO Examiner on Apr. 13, 2016; 29 printed pages.

"Office Action" and "Examiner Initiated Interview Summary" issued in related US. Appl. No. 14/383,802 dated Apr. 20, 2016; Publisher: USPTO; Country: US.

"Final Office Action" dated Oct. 31, 2016 in related patent U.S. Appl. No. 14/383,802.

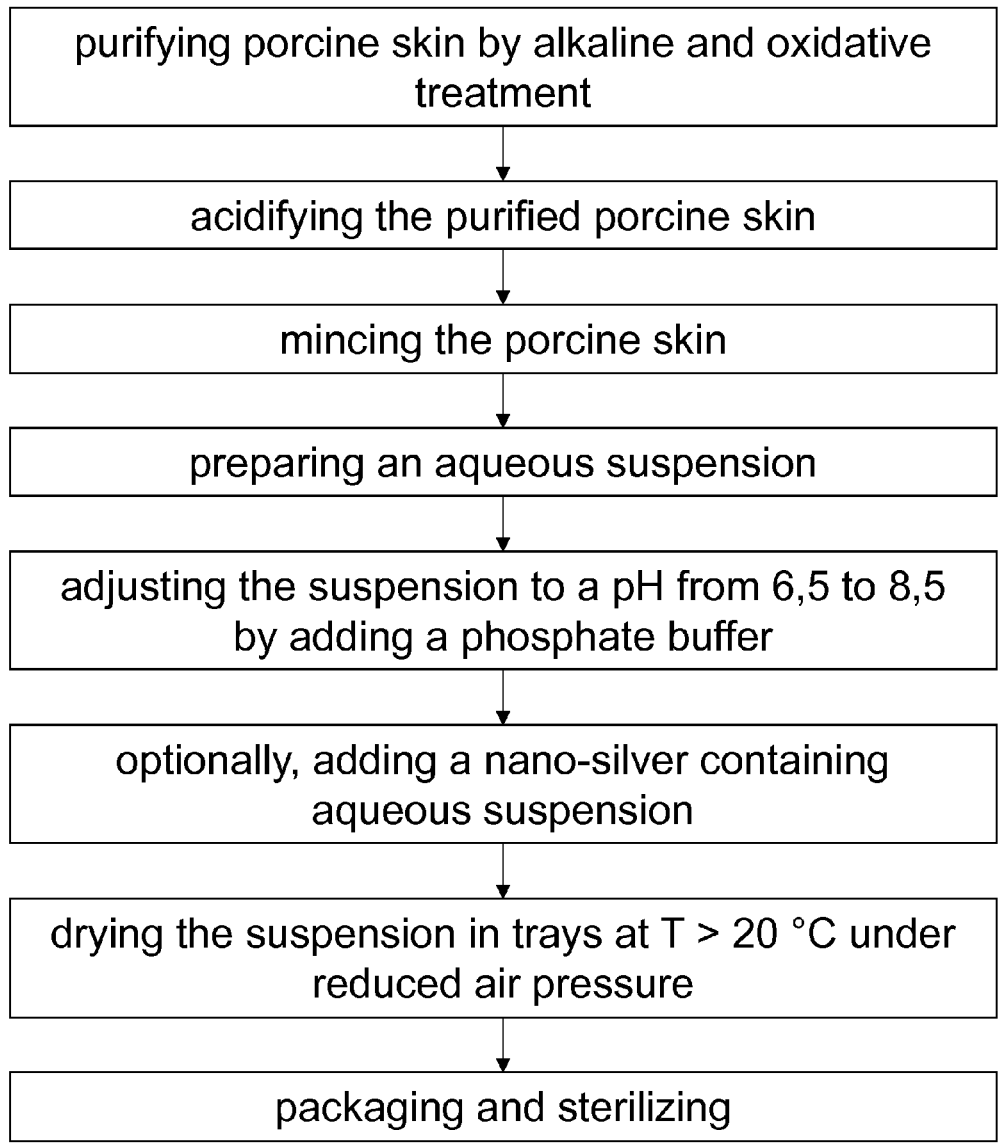

METHOD FOR PRODUCING COLLAGEN-CONTAINING SHEET MATERIAL

FIELD OF THE INVENTION

The invention relates to a collagen-containing sheet material used as a wound dressing, in particular for surgical procedures.

BACKGROUND OF THE INVENTION

Collagen-containing sheet materials are known. For example, published patent application EP 2 098 255 A2 (AAP Biomaterials GmbH) discloses a method for producing collagen material. As a starting material, porcine skin is used, which is purified by an alkaline, oxidative, and acidic treatment to remove grease and other foreign matter.

The porcine skin is comminuted mechanically, and subsequently an aqueous suspension is produced from the porcine skin, which is adjusted to a neutral to slightly alkaline pH by addition of a phosphate buffer.

Thereby, a three-dimensional network of collagen fibrils is formed. The suspension containing this network is lyophilized. The resulting sponge-like or non-woven sheet material is highly porous, very flexible, and does not adhere to surgical instruments, in both its dry and wet states.

For some applications, a drawback of the material is that it can be badly cut in the rehydrated state, due to its very high flexibility. Further, the material swells in the wet state.

In some applications it is particularly disadvantageous that the sheet material is opaque. So the surgeon cannot look through the sheet material, which would strongly facilitate accurate placement of the sheet material in many cases.

SUMMARY OF THE INVENTION

The invention is therefore based on the object to at least mitigate the drawbacks of the prior art mentioned above.

A particular object of the invention is to provide a flexible sheet material which at the same time is transparent to a certain extent, so that at least in its applied state the tissue below is discernable.

The object of the invention is already achieved by a method for producing a collagen-containing sheet material and by a transparent collagen-containing sheet material in accordance with the illustrative embodiment of the present invention.

The invention relates to a method for producing a collagen-containing sheet material. A collagen-containing sheet material in particular refers to a material which comprises more than 70%, preferably more than 90% of collagen.

The manufacturing method comprises wet-chemical preparation of a starting material from mammalian skins.

Preferably, porcine skin is used as a starting material. However, it is also conceivable to use equine or bovine starting materials.

The alkaline, oxidative, and acidic treatment may be performed, for example, by alternately dipping and rinsing in bases, peroxides, and acids. In particular sodium hydroxide, hydrogen peroxide, and phosphoric acid may be used.

The wet-chemical preparation is performed in order to remove undesired foreign material, such as grease, cell components, and pyrogens, and to eliminate microbial organisms.

Following the wet-chemical treatment, the starting material is preferably acidified.

For producing a collagen-containing suspension, the starting material is comminuted. Comminuting is preferably performed mechanically, especially by mincing and/or in a rotor-stator type mill.

Comminuting is preferably performed following the wet-chemical preparation. However, it is also conceivable, to first comminute the starting material and to subsequently perform the wet-chemical treatment.

In particular by mechanical comminution of the starting material a suspension is provided which includes a native collagen in which the telopeptides are largely preserved.

According to the invention, the suspension is then dried, wherein in contrast to the procedure described in published patent application EP 2 098 255 A2 the drying is performed in a manner so that the collagen at least partially settles before or during the drying and forms a transparent skin.

So the material produced is not highly porous, but has a dense film-like structure which is at least partially transparent.

Transparent in the sense of the invention does not mean that the material is completely transparent like a clear transparent glass pane or film, but that the material is translucent to an extent that at least in its applied state the underlying tissue is visible. It will be understood that the material may contain air bubbles and haziness.

The drying may be performed by first waiting until most of the collagen has settled.

Further, the drying may be performed in particular at temperatures above the freezing point of the suspension. This causes the collagen material to sag together during drying to form a film-like sheet material. It is also conceivable to perform drying under reduced pressure.

Surprisingly, the sheet material so produced is bendable and flexible. Previously it was assumed that a porous three-dimensional structure would be necessary in order to provide a material which is not brittle and fragile.

Surprisingly, however, the invention enabled to provide a material which is translucent and flexible. Furthermore, in contrast to a highly porous non-woven or spongy material, the material can be easily cut in the rehydrated state, so that the user may easily adjust the shape and size of the material.

In a further embodiment of the invention, metal particles, in particular silver particles, are added to the suspension.

The addition of an elemental metal makes it possible to functionalize the material with further properties. Silver is preferably used to provide antibacterial properties.

It has been found that the film-like material of the invention releases metal ions more slowly as compared to a porous material, so that the effect lasts longer and toxic concentrations directly after application can largely be avoided.

A further advantage of the use of elemental silver as compared to the use of metal salts is that dark staining will only occur to a slight extent, if any.

In order to provide a long lasting antibacterial effect, or for other purposes, is also conceivable to add other active substances, such as bacteriostatic or bactericidal agents or antifungal agents, such as gentamicin or guanidines.

The metal particles are preferably added in form of a suspension.

In particular, particles with an average particle size from 10 nm to 10 μm may be used. Preferably nanoparticles are used, especially nanoparticles with a particle size of less than 50 nm.

In fact, agglomeration phenomena may arise with such nanomaterials in the manufacturing of the sheet material, so that the metal in the sheet material is mainly present in agglomerates. However, this does not affect the positive properties of the material according to the invention.

In a preferred embodiment of the invention, the metal is dosed such that the sheet material produced has a metal content from 10 to 10,000 ppm, preferably from 100 to 10,000 ppm.

In a preferred embodiment of the invention, before drying the pH of the suspension is adjusted to a value between 3 and 9, preferably between 5.5 and 8.

It is especially contemplated adjust the suspension to a neutral to slightly alkaline pH.

To avoid a reaction of the silver with chlorine, the suspension should not be acidified using hydrochloric acid. Preferably, a substantially chloride-free suspension is used.

The material of the invention may be produced without the use of a crosslinking agent. However, the invention does not exclude the use of a crosslinking agent.

The invention further allowed to simplify the drying. Lyophilization is not necessary, but may yet be performed when the collagen has settled. Preferably, the material is dried under reduced pressure at a temperature above the freezing point of the suspension.

The invention permits to provide an at least partially transparent collagen-containing sheet material.

This sheet material preferably has a closed porosity of less than 50%, more preferably less than 20%.

The material has a film-like structure and is thinner than similarly stable non-woven or sponge-like collagens. In particular, the sheet material has a thickness from 0.05 to 2.00 mm, preferably between 0.1 and 1.00 mm.

The material may take various shapes, in particular round, square, and oval shapes.

It will be understood that typically a sterile material will be prepared. Sterilization may be accomplished by ionizing radiation, e.g. y- and/or p-irradiation.

Preferably, sterilization is performed using ethylene oxide, since as a result thereof the stability of the sheet material is increased, whereas at least strong ionizing radiation weakens the stability of the sheet material.

Possibly, the ethylene oxide causes additional crosslinks to be formed.

To obtain antibacterial properties, in particular a nano-silver containing suspension is used, which contains an emulsifier.

A method for producing such a stable silver containing suspension is known from published patent application DE 10 2009 059 276 A1 (Rent-a-Scientist GmbH). The disclosure of this document is fully incorporated herein by reference.

The inventive material has hemostatic properties, and due to its antibacterial properties it is especially suitable for use in conjunction with poorly healing wounds, in particular in case of diabetes and for burn injuries. Also dental applications are conceivable.

DESCRIPTION OF THE DRAWINGS

FIG. 1 shows a flowchart of a method for producing a collagen-containing sheet material.

DETAILED DESCRIPTION

First, porcine skin is prepared by an alkaline, oxidative, and acidic treatment.

For this purpose, hydrogen peroxide, sodium hydroxide, and phosphoric acid may be used, for example, in which the starting material is alternately dipped and is then rinsed.

Through this wet-chemical preparation, a starting material is provided which comprises more than 70%, preferably more than 80% of collagen.

Then, the wet-chemically purified porcine skin is acidified. Preferably, phosphoric acid is used for this purpose.

To prepare a suspension, the porcine skin is first comminuted mechanically by mincing, and then an aqueous suspension is produced from the slurry resulting from further comminuting steps. This suspension in particular has a solids content from 0.5 to 5%.

Then, the aqueous suspension is adjusted to a neutral to slightly alkaline pH from 6.5 to 8.5 by adding a phosphate buffer.

Subsequently, a nano-silver containing aqueous suspension may be added. For this purpose, a suspension should be used which is stable over a longer period. The metal is not added as a salt, but as elemental silver.

To achieve a good distribution, the addition of the nano-silver containing suspension may be accomplished using suitable dispersion promoting means, for example in an ultrasonic bath, or a suitable rotor-stator type mill.

Subsequently, the suspension is dried in trays at a temperature above 20° C. under reduced pressure.

The collagen will thereby mostly settle on the bottom of the tray as a film-like structure, with a large part of the silver particles trapped in the material being formed.

Subsequently, the dried sheet material can be packaged and sterilized.

Sterilization may be accomplished using ethylene oxide, for example.

Also, sterilization of the already packaged material is possible by irradiation.

The produced material rehydrates very fast, has a good hemostatic effect, and is bendable, rollable and can be cut easily, even in its dry state.

Additionally, the material is translucent at least to an extent so that the applied material permits to perceive the underlying tissue. Complications such as inflammation arising under the sheet material can be easily identified.

Furthermore, the material is less prone to sticking and can be easily removed.

What is claimed is:

1. A method for producing a collagen-containing sheet material, comprising:
    treating a mammalian skin starting material with wet chemicals;
    mechanically comminuting the treated starting material into a slurry;
    preparing an aqueous suspension of the comminuted, treated starting material from the slurry, said aqueous suspension having a solid content from 0.5 to 5%;
    adjusting the pH of the aqueous suspension to a pH between 5.5 and 8;
    transferring the aqueous suspension to a tray;
    waiting until at least a portion of the suspension in the tray settles out before drying; and
    drying the aqueous suspension in the tray such that a transparent film of the collagen-containing sheet material is formed having a closed porosity of less than 20%;
    wherein said collagen-containing sheet material comprises more than 70% of collagen; and
    wherein said collagen-containing sheet material has a thickness between 0.05 and 2 mm.

2. The method for producing a collagen-containing sheet material as claimed in claim 1, wherein metal particles are added to the aqueous suspension.

3. The method for producing a collagen-containing sheet material as claimed in claim 2, wherein metal particles are added as a suspension.

4. The method for producing a collagen-containing sheet material as claimed in claim 2, wherein silver particles are added to the aqueous suspension.

5. The method for producing a collagen-containing sheet material as claimed in claim 2, wherein the metal particles have an average particle size of less than 50 nm.

6. The method for producing a collagen-containing sheet material as claimed in claim 1, wherein metal particles are added, which have an average particle size between 10 nm and 10 µm.

7. The method for producing a collagen-containing sheet material as claimed in claim 1, wherein bactericidal agents are added to the aqueous suspension.

8. The method for producing a collagen-containing sheet material as claimed in claim 1, wherein antifungal agents are added to the aqueous suspension.

* * * * *